US00PP37244P2

(12) United States Plant Patent
Sapia

(10) Patent No.: US PP37,244 P2
(45) Date of Patent: Feb. 3, 2026

(54) ***HELICHRYSUM* PLANT NAMED 'HYBHS23157'**

(50) Latin Name: ***Helichrysum panormitanum* x *doerflerii* x *italicum***
Varietal Denomination: HYBHS23157

(71) Applicant: KLEMM + SOHN GMBH & CO. KG, Stuttgart (DE)

(72) Inventor: Flavio Sapia, Sanremo (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/774,069

(22) Filed: Jul. 16, 2024

(51) Int. Cl.
*A01H 6/14* (2018.01)
*A01H 5/02* (2018.01)

(52) U.S. Cl.
USPC ..... Plt./359

(58) Field of Classification Search
USPC ..... Plt./359
CPC ..... A01H 6/14; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Helichrysum* plant particularly distinguished by medium sized leaves with a gray-green color; and an upright plant habit with a medium or average height, is disclosed

1 Drawing Sheet

Genus and species: *Helichrysum panormitanum* x *doerflerii* x *italicum*.
Variety denomination: 'HYBHS23157'.

BACKGROUND OF THE NEW PLANT

The present invention comprises a new and distinct variety of *Helichrysum*, botanically known as *Helichrysum panormitanum* x *doerflerii* x *italicum* and hereinafter referred to by the variety name 'HYBHS23157'. 'HYBHS23157' originated from a cross conducted in in July 2016 in Sanremo, Italy between the female *Helichrysum* 'HEL014-13' (unpatented) and the male *Helichrysum* 'HEL006-15' (unpatented).

The seeds from the cross were sown and plants were grown outdoors for evaluation, where an individual plant designated 'HYBHS23157' was selected from the group of plants in April 2017. In August 2017 in Sanremo, Italy, 'HYBHS23157' was first vegetatively propagated by stem cuttings. 'HYBHS23157' was found to reproduce true to type in successive generations of asexual propagation via stem cuttings.

SUMMARY

The following are the most outstanding and distinguishing characteristics of this new variety when grown under normal horticultural practices in Sanremo, Italy and Stuttgart, Germany.

1. Medium sized leaves with a gray-green color; and
2. Upright plant habit with a medium or average height.

DESCRIPTION OF THE PHOTOGRAPH

This new *Helichrysum* plant is illustrated by the accompanying photograph which shows the plant's overall plant habit including form, and foliage. The photograph is of a 15-week-old plant grown in a greenhouse in a 12 cm pot in Stuttgart, Germany in November 2023. The colors shown are as true as can be reasonably obtained by conventional photographic procedures.

DESCRIPTION OF THE NEW VARIETY

The following detailed descriptions set forth the distinctive characteristics of 'HYBHS23157'. The data which define these characteristics were collected in Stuttgart, Germany in November 2023 on 15-week-old plants grown in a 12 cm pot in a glass greenhouse with a pinch date one week after potting. Color references are to The R.H.S. Colour Chart of The Royal Horticultural Society of London (R.H.S.), 5$^{th}$ edition (2007).

Classification:
- *Family*.—Asteraceae.
- *Botanical*.—*Helichrysum panormitanum* x *doerflerii* x *italicum*.
- *Common*.—Italian strawflower.
- *Designation*.—'HYBHS23157'.

Parentage:
- *Female parent*.—*Helichrysum* 'HEL014-13' (unpatented).
- *Male parent*.—*Helichrysum* 'HEL006-15' (unpatented).

Plant:
- *Habit*.—Upright.
- *Height*.—16.0 cm to 19.0 cm.
- *Spread*.—20.0 cm to 25.0 cm.
- *Life cycle*.—From February to October.
- *Time to produce a rooted cutting*.—3 to 4 weeks.
- *Root description*.—Fine, white, RHS 196D to light brown RHS 199D, freely branching and dense.
- *Time to get a finished product*.—10 weeks.
- *Lastingness of inflorescence on the plant*.—No flowers have been observed.
- *Propagation type*.—Vegetative via cuttings.

Lateral branches:

*Number of branches per plant.*—12 to 18 depending on pinching, branches are strong, grow initially lateral to became more vertical during growing, depending by age can show shoots in the lower part at leaf insertion.

*Color.*—RHS 155C.

*Pubescence.*—Present.

*Stem form.*—Round.

*Diameter.*—3.0 mm to 4.0 mm.

*Length.*—15.0 cm to 20.0 cm.

*Internode length.*—1.0 cm to 1.4 cm.

*Anthocyanin.*—Absent.

Foliage:

*Arrangement.*—Alternate.

*Length.*—3.5 cm to 10.0 cm (very old leaves), average foliage is 5.0 cm.

*Width.*—0.5 cm to 1.3 (very old leaves), average is 0.7 cm.

*Shape.*—Obovate.

*Apex.*—Acute.

*Base.*—Auriculate.

*Margin.*—Entire.

*Surface texture.*—Upper surface: Pubescence, hoary. Lower surface: Pubescence, hoary.

*Color, immature leaves.*—Upper surface: RHS 155C and 196D. Lower surface: RHS 196D.

*Color, mature leaves.*—Upper surface: RHS 189B. Lower surface: RHS 189B.

*Venation pattern.*—Hyphodromous.

*Venation color.*—Upper surface: RHS 196D. Lower surface: RHS 196D.

*Petiole.*—No petioles observed.

Disease and pest/insect resistance: No disease and pest/insect resistance observed.

COMPARISON WITH PARENTAL LINES AND KNOWN VARIETY

'HYBHS23157' is distinguished from its parents as described in Table 1.

TABLE 1

Comparison with Parental Lines

| Trait | Variety 'HYBHS23157' | Female parent | Male Parent |
|---|---|---|---|
| Leaves | Medium sized leaves | Smaller leaves than 'HYBHS23157' | Larger leaves than 'HYBHS23157' |
| Leaves color | Grayed green color | Greenish color | Grayed green color |
| Plant height | Medium | Medium | Taller than 'HYBHS23157' |

'HYBHS23157' is most similar to the *Helichrysum italicum* 'HYBHS18538' (U.S. Plant Pat. No. 30,649). Differences between the varieties are described in Table 2.

TABLE 2

Comparison with Similar Variety

| Characteristic | 'HYBHS23157' | 'HYBHS18538' |
|---|---|---|
| Habitus | Upright | Spreading |
| Speed of growth | Medium | Faster than 'HYBS23157' |

I claim:

1. A new and distinct cultivar of *Helichrysum* plant designated 'HYBHS23157' as illustrated and described herein.

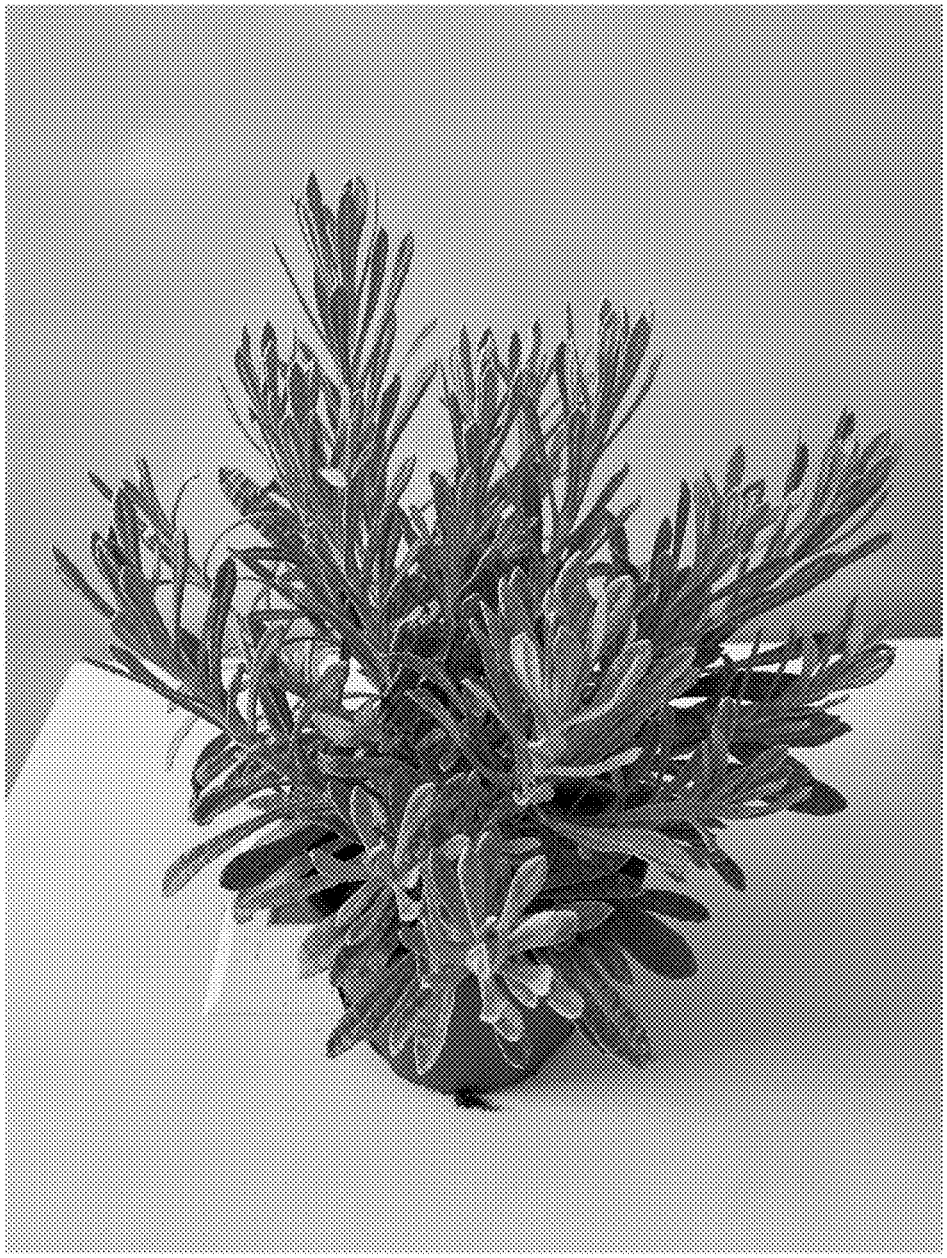

* * * * *